(12) United States Patent
Stegmeier et al.

(10) Patent No.: US 12,029,593 B2
(45) Date of Patent: Jul. 9, 2024

(54) X-RAY HIGH-VOLTAGE GENERATOR HAVING A TWO-PHASE COOLING SYSTEM

(71) Applicant: Siemens Healthcare GmbH, Erlangen (DE)

(72) Inventors: Stefan Stegmeier, Munich (DE); Florian Schwarz, Fuerth (DE); Stefan Waffler, Buckenhof (DE); Thomas Weidinger, Erlangen (DE); Andreas Hader, Erlangen (DE); Michael Wimmer, Weisendorf (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/186,297

(22) Filed: Mar. 20, 2023

(65) Prior Publication Data
US 2023/0293123 A1    Sep. 21, 2023

(30) Foreign Application Priority Data

Mar. 21, 2022   (DE) .................... 10 2022 202 726.4

(51) Int. Cl.
*A61B 6/00*   (2024.01)
*A61B 6/03*   (2006.01)
(52) U.S. Cl.
CPC ............ *A61B 6/035* (2013.01); *A61B 6/4488* (2013.01)
(58) Field of Classification Search
CPC ......... A61B 6/035; A61B 6/4488; H05G 1/10
See application file for complete search history.

(56) References Cited

U.S. PATENT DOCUMENTS

| | | | |
|---|---|---|---|
| 7,576,330 B1 | 8/2009 | Lacey et al. | |
| 2004/0264222 A1 | 12/2004 | Beland | |
| 2020/0008287 A1 | 1/2020 | Heuft | |
| 2021/0204385 A1* | 7/2021 | Chen ................ | H05G 1/04 |

FOREIGN PATENT DOCUMENTS

| | | |
|---|---|---|
| CN | 108447755 A | 8/2018 |
| CN | 110383954 A | 10/2019 |
| CN | 211606905 U | 9/2020 |

(Continued)

OTHER PUBLICATIONS

Schwarz F. et al.:"Thermodynamic Analysis of the Dryout Limit of Oscillating Heat Pipes", Energies 2020, 13(23), 6346; https://doi.org/10.3390/en13236346.

(Continued)

*Primary Examiner* — Dani Fox
(74) *Attorney, Agent, or Firm* — Harness, Dickey & Pierce, P.L.C.

(57) ABSTRACT

An X-ray high-voltage generator comprises: a circuit arrangement having at least one power electronics circuit part, wherein the at least one power electronics circuit part is configured to form a heat source during operation; and a two-phase cooling system having a heat sink. The at least one power electronics circuit part is directly thermally coupled to the two-phase cooling system to cool the heat source at the heat sink. The two-phase cooling system has a cooling element block that spatially surrounds a cooling channel circuit. The cooling channel circuit is at least partially filled with a working medium, and is configured to act as a heat pipe.

20 Claims, 8 Drawing Sheets

(56) References Cited

FOREIGN PATENT DOCUMENTS

| | | |
|---|---|---|
| DE | 102009003792 A1 | 11/2009 |
| DE | 112018000018 T5 | 12/2018 |
| EP | 1102388 A2 | 5/2001 |
| WO | WO 03049138 A2 | 6/2003 |

OTHER PUBLICATIONS

Taft B.S et al.:"Non-Condensable Gases and Oscillating Heat Pipe Operation", Frontiers in Heat Pipes (FHP), 4, 013003 (2013).

Der O., Marengo M. et al.:"Thermal performance of pulsating heat stripes (PHS) built with plastic materials", Joint 19th IHPC and 13th IHPS, Pisa, Italy, Jun. 10-14, 2018.

Yang K.S. Tsung-Yi et al.:2A novel flat polymer heat pipe with thermal via for cooling electronic devices, Energy Conversion and Management 100 (2015) 37-44.

Der O., Alqahtani A. et al.:"Characterization of polypropylene pulsating heat stripes: Effects of orientation, heat transfer fluid, and loop geometry", Applied Thermal Engineering 184 (2021) 116304.

Schwarz F. et al.."Interaction of flow pattern and heat transfer in oscillating heat pipes for hot spot applications", Applied Thermal Engineering vol. 196, Sep. 2021, 117334, DOI: https://doi.org/10.1016/j.applthermaleng.2021.117334.

German Office Action for German Application No. 10 2022 202 726.4 and English translation thereof dated Nov. 29, 2022.

German Decision to Grant for German Application No. 10 2022 202 726.4 and English translation thereof dated Nov. 6, 2023.

Chu, Xiaoyang ; "Overview of cooling and heat dissipation systems in medical equipment" Jul. 25, 2018: China Medical Device Information;.

Xu, Ruiqiang ; "Application of smart fan technology in cooling X-ray tube components"; Jan. 25, 2017; Modern Business Trade Industry;.

\* cited by examiner

X-RAY HIGH-VOLTAGE GENERATOR HAVING A TWO-PHASE COOLING SYSTEM

CROSS-REFERENCE TO RELATED APPLICATION(S)

The present application claims priority under 35 U.S.C. § 119 to German Patent Application No. 10 2022 202 726.4, filed Mar. 21, 2022, the entire contents of which are incorporated herein by reference.

FIELD

One or more example embodiments of the present invention relate to an X-ray high-voltage generator, an X-ray tube assembly and a computed tomography facility.

BACKGROUND

A conventional X-ray high-voltage generator is typically used to generate high voltage in the kV range from a conventional mains voltage. This high voltage is applied, for example, between an electron emitter and an anode of an X-ray tube, with electrons emitted by the electron emitter being accelerated by the high voltage to kinetic energies in the keV range and generating X-ray beams on interaction with the anode.

Such an X-ray high-voltage generator outputs a comparatively high electrical peak power at the X-ray tube during the period of X-ray beam generation. The electrical peak power lies in the range of several kW as a function of the respective application. In the period between X-ray beam generation the X-ray high-voltage generator typically outputs no or only a very low electrical average power. The X-ray high-voltage generator is usually adapted therefore to provide a high peak power with a low average power output.

This kind of configuration of the X-ray high-voltage generator makes high demands on a cooling system of the X-ray high-voltage generator, because a correspondingly high power loss input usually results in the X-ray high-voltage generator during output of the electrical peak power. In order to not overheat the power electronics circuit parts provided in the X-ray high-voltage generator for providing the high voltage, the power loss converted to heat has to be at least partially, preferably completely, dissipated by the cooling system.

A further challenge is that the power electronics circuit parts, which are frequently simultaneously operated in the X-ray high-voltage generator, are preferably connected to a heat sink of the cooling system as uniformly as possible. The heat has to be transported partially over sections of varying length in the process. The circuit part, which can be cooled the least, for example owing to the greatest distance from the heat sink of the cooling system, typically defines the capacity of the entire X-ray high-voltage generator in this connection.

For example, a conventional cooling system can be dimensioned in such a way as to be able to permanently dissipate the maximum power loss. It is known to configure the cooling system of a conventional X-ray high-voltage generator accordingly with temporary heat accumulators to be able to temporarily store the lost heat due to the thermal capacity created thereby. For example, a performance category of the cooling system can be set by way of a specific configuration of the temporary heat accumulator. Such a temporary heat accumulator is preferably arranged close to the heat source, in particular the power electronics component. A temporary storage block, for example, having high thermal capacity, for example made of copper and/or aluminum, is suitable as a temporary heat accumulator. The temporary heat accumulator is usually connected to the heat source by as few thermal transitions as possible. Due to the thermal capacity of the temporary heat accumulator the power loss input that accrues during X-ray beam generation can preferably be temporarily stored, whereupon the thermal energy buffered in the temporary heat accumulator is typically dissipated to an external cooling medium with a higher time constant. For this, the power loss is dissipated, for example via a supporting plate, to a heat sink, which can form, for example, a gantry of a computed tomography facility.

Such a conventional cooling system having a temporary heat accumulator has a comparatively complex structure, which can be composed of a plurality of elements, such as fixing plates, a temporary storage block and power electronics circuit parts. The conventional cooling system is therefore frequently comparatively large and/or heavy, and this can be cost-intensive owing to the material usage. Even narrow manufacturing tolerances that are mutually dependent in particular place high demands on the cooling system and the assembly process thereof.

SUMMARY

One or more example embodiments of the present invention are based on at least the object of disclosing an X-ray high-voltage generator, an X-ray tube assembly and a computed tomography facility having a more flexible and more powerful cooling system.

At least this object is achieved by the features of the independent claims, dependent claims and/or the embodiments discussed herein.

An inventive X-ray high-voltage generator for providing a high voltage for X-ray beam generation in an X-ray tube has
- a circuit arrangement having at least one power electronics circuit part, wherein the at least one power electronics circuit part forms a heat source during operation, characterized by
- a two-phase cooling system having a heat sink, wherein the at least one power electronics circuit part is directly thermally coupled to the two-phase cooling system for dissipating heat from the heat source at the heat sink, wherein the two-phase cooling system has a cooling element block, wherein the cooling element block spatially surrounds a cooling channel circuit, wherein the cooling channel circuit is at least partially filled with a working medium and acts as a heat pipe.

The two-phase cooling system makes the following advantages possible in particular:
Advantageously a spatial isolation of the heat sink and the heat source by use of the two-phase cooling system can be achieved, whereby the construction of the X-ray high-voltage generator becomes more flexible. In particular the configuration of the cooling element block with the inner cooling channel circuit makes it possible to overcome greater distances between the heat source and the heat sink typically without impairing the cooling capacity of the two-phase cooling system. The two-phase cooling system, in particular the cooling channel circuit and the cooling element block, therefore makes a spatial flexibilization possible because, in contrast to conventional X-ray high-voltage generators, very remote heat sinks can now be advantageously thermally directly coupled. As an alternative or in addition, the spatial flexibilization advantageously makes a more flexible shaping possible in the configuration of the outer form of the two-phase cooling system, in particular of the cooling element block.

A further advantage of the X-ray high-voltage generator relates to the possibility of being able to integrate different functions in the two-phase cooling system, in particular in the cooling element block. These functions comprise, for example in addition to heat dissipation, electrical insulation, a distance compensation, a housing (part), an interface function and/or a shielding. Advantageously at least one further conventional component, which is typically required for these functions, is consequently omitted. The integration of these functions or some of these functions in the two-phase cooling system can simplify and/or shorten a manufacturing process of the X-ray high-voltage generator, moreover, since typically fewer conventional components have to be assembled. This is frequently accompanied by a cost benefit. The distance can be compensated by a custom-made configuration of the cooling element block. The housing function can be achieved in that the housing and the cooling element block are manufactured in one step. The manufacturing option using injection molding or 3D-printing results in usually simpler integration possibilities than with conventional sheets. The shielding function can be achieved, in particular, by way of at least partial coating of the cooling element block, for example by a fluid-tight, in particular shielding or conductive, layer or by a metal element. The interface function can preferably be achieved in that a current conduction, for example a busbar for high currents, a holding apparatus and/or a fixing element are introduced into the cooling element block. An advantage of using the two-phase cooling system in the X-ray high-voltage generator is that, in principle, the two-phase cooling system can function in a vacuum.

The X-ray high-voltage generator is designed for providing high voltage in particular at an output of the X-ray high-voltage generator. Providing the high voltage comprises, in particular, generating the high voltage. During provision the X-ray high-voltage generator transforms, in particular, an input-side, conventional mains voltage, which does not typically lie in the kV range but below it, or a direct current link voltage into high voltage. The high voltage is typically applied at the output of the X-ray high-voltage generator. The high voltage is typically greater than 10 kV and/or less than 200 kV, is, for example, between 20 and 150 kV, in particular between 70 to 120 kV. The X-ray high-voltage generator, for example the output, can be connected to the X-ray tube, in particular an input of the X-ray tube, via a high voltage cable, typically for transferring the high voltage. The X-ray tube can generate the X-ray beams, in particular as a function of the high voltage provided by X-ray high-voltage generator. The generated X-ray beams typically have an energy spectrum up to the value of the high voltage multiplied by the elementary charge e. The X-ray beams are typically not generated in the X-ray high-voltage generator but in the X-ray tube.

The high voltage is provided, in particular, via the circuit arrangement. The circuit arrangement comprises at least one power electronics circuit part for the provision, in particular the generation, of the high voltage. The circuit arrangement usually also comprises further electronic component parts and/or power electronics circuit parts. The at least one power electronics circuit part can be, for example, a power transistor, a power electronics component, an inductive component, a capacitive component and/or a resistive component. The at least one power electronics circuit part can be installed, in particular, in a TO-247 housing, an SMD housing, a THT housing or a power module.

The high voltage is typically provided during operation of the X-ray high-voltage generator. During operation, usually the at least one power electronics circuit part of the circuit arrangement is operative, in particular under load. Operation of the at least one power electronics circuit part requires the use of electrical power, with usually only part of the electrical power being provided in the form of the high voltage and a further part decaying as power loss. The at least one power electronics circuit part is a heat source at least during operation. The power loss input is typically so high that during operation the heat source is cooled by the two-phase cooling system. The power loss input can vary during operation. In particular after provision of the high voltage, the at least one power electronics circuit part can continue for a certain period as a heat source to be cooled.

The two-phase cooling system comprises the heat sink and/or acts as a heat sink. The heat sink is suitable, in particular, for dissipating some of the power loss input converted into heat. The heat sink typically emits more power loss to an environment outside of the two-phase cooling system than the heat sink absorbs from the environment. The heat sink is at least one section of the two-phase cooling system, which is suitable for heat dissipation, for example owing to the material composition, of the inner construction and/or the outer form. The outer form of the heat sink can have a surface enlargement, for instance by way of cooling ribs or cooling fins. The heat sink be a passive component or an active component, configured, for example, with a fan. The heat sink can be actively or passively operated. The heat sink can be connected to the cooling element block and/or be directly thermally coupled to the cooling element block.

The heat sink is typically remote from the heat source in such a way that the transferred heat is dissipated away from the heat source. Heat dissipation of the heat source comprises, in particular, cooling of the heat source. The heat sink is directly thermally coupled for example to a gaseous or liquid external cooling circuit, for intensifying heat dissipation. In this case, the external cooling circuit, in particular, forms the environment of the heat sink and the heat sink typically acts as a heat exchanger at the external cooling circuit. The external cooling circuit can be formed, in particular, by an electrically insulating fluid, in particular oil, in which the X-ray high-voltage generator, the circuit arrangement and/or the at least one power electronics circuit part is mounted. The heat transfer in the external cooling circuit can be based on forced convection.

The two-phase cooling system can be designed, in particular, for heat dissipation of the further electronic component parts and/or the power electronics circuit parts. The two-phase cooling system can be adapted, in particular, to dissipate heat from a heat source at a heat sink, a plurality of heat sources at a heat sink, a heat source at a plurality of heat sinks or a plurality of heat sources at a plurality of heat sinks.

"Directly thermally coupled" means, in particular, that two elements are typically physically connected together for a heat transfer. For example, the at least one power electronics circuit part is connected to the two-phase cooling system or attached to the two-phase cooling system.

The cooling element block of the two-phase cooling system has, for example, metal, ceramic and/or a polymer. Preferred embodiments of the cooling element block comprise a configuration made of ceramic or a configuration made of a polymer. Particularly preferred is the embodiment where the cooling element block is composed of a polymer and thus forms a polymer cooling element block. The polymer cooling element block has the advantage, in particular, of lower costs, a lower weight and/or simpler processing compared to metal. Furthermore, polymers are usually electrically insulating and/or amagnetic. The ceramic can be composed, in particular of Al2O3, Si3N or AlN. The metal can be, in particular, copper, aluminum, iron or alloys of these elements. One advantage of the design made of ceramic and/or metal can be that the cooling element block is fluid-tight. The polymer can be, in particular, polypropylene, polycarbonate, polyetheretherketone, polyamide or acrylonitrile-butadiene-styrene copolymer. The cooling element block can be produced by an additive manufacturing process and/or an injection molding manufacturing process.

A cooling channel circuit is provided in the cooling element block. The cooling element block typically surrounds the cooling channel circuit completely, so the working medium is substantially kept away from a channel wall of the cooling channel circuit in the cooling channel circuit. "Substantially" refers to the fact that a certain diffusion of the working medium can occur through the channel wall as a function of the material composition of the cooling element block and/or a certain porosity of the cooling element block.

The cooling element block can basically be designed as part of a housing of the X-ray high-voltage generator. In this case, a surface opposing the at least one power electronics circuit part typically forms the heat sink. A further advantage of the cooling element block can be if a holding apparatus for a metal element, for example a printed circuit board, a fixing element and/or for a current supply is provided as part of the cooling element block.

The cooling channel circuit comprises a self-contained path along which the working medium travels back and forth, in particular oscillates, during operation. In this case, the cooling channel circuit typically acts as an oscillating heat pipe. The term "pulsating" can be used in this context instead of oscillating. The cooling channel circuit has, in particular, a plurality of straight and/or bent channel sections. The channel sections can be arranged in a circular, meandering, spiral, planar, elongated and/or angular manner. The number of channel sections per unit area can be increased, in particular, in the region of the heat sink and/or the heat source.

The channel sections have, for example, a diameter less than 6 mm, preferably less than 3 mm. A cross-section of the channel sections is, for example, between 0.1 and 50 mm^2, preferably between 0.25 and 4 mm^2. The channel sections are typically designed to make a capillary flow possible or designed by capillarity, in particular if the heat pipe is designed as an oscillating heat pipe. Gas and liquid phases are separate from each other due to the dominant surface tension in this case. The channel sections typically have a closed, for example tubular, in particular round or (rect-) angular, cross-section. During operation the working medium oscillates back and forth in the cooling channel circuit. The working medium can typically have a preferred direction of flow.

The two-phase cooling system is characterized in that the cooling channel circuit has a first section facing the heat source and a second section facing the heat sink. At the first section the cooling channel circuit typically absorbs at least some of the power loss input and at the second section transfers at least some of the power loss input to the heat sink. For example, the working medium evaporates at the first section, also called an evaporator, and condenses at the second section, also called a condenser. The heat is transported in particular due to a phase change with repeatable change between gas phase and liquid phase, therefore. The heat pipe can be, in particular, an oscillating heat pipe, which uses the phase change and a convective heat transport. Alternatively, what is known as a "vapor chamber" technique can be used. The heat pipe can alternatively work with gravity to return the gaseous working medium to the evaporator. In this case, the two-phase cooling system is a kind of thermosiphon.

Reference is made in respect of the basic mode of operation and configuration of a heat pipe to the publications by Taft, "Non-Condensable Gases and Oscillating Heat Pipe Operation", Frontiers in Heat Pipes (FPH), 4, 013003 (2013), DOI: 10.5098/fhp.v4.1.3003, Yang et al., "A novel flat polymer heat pipe with thermal via for cooling electronic devices", Energy Conversion and Management 100 (2015) 37-44, DOI: 10.1016/j.enconman.2015.04.063, Schwarz et al., "Interaction of flow pattern and heat transfer in oscillating heat pipes for hot spot applications", Applied Thermal Engineering Volume 196, September (2021), 117334, DOI: https://doi.org/10.1016/j.applthermaleng.2021.117334, Schwarz et al., "Thermodynamic Analysis of the Dryout Limit of Oscillating Heat Pipes", Energies 13, no. 23: 6346. https://doi.org/10.3390/en13236346, Der et al., "Characterization of polypropylene pulsating heat stripes: Effects of orientation, heat transfer fluid, and loop geometry", Applied Thermal Engineering 184 (2021) 116304, DOI: 10.1016/j.applthermaleng.2020.116304 and Der et al., "Thermal performance of pulsating heat stripes (PHS) built with plastic materials", Joint 19th IHPC and 13th IHPS, Pisa, Italy, Jun. 10-14, 2018.

The cooling channel circuit can be partially filled with the working medium. The filling level of the cooling channel circuit is typically between 10 and 90%, preferably between 30 and 80%. The filling level is defined as a function of the proportion of the working medium present in the liquid state relative to the volume. The remaining part of the volume is filled with working medium in the gaseous state, in particular during operation. The cooling channel circuit can have a sealable opening for regulating the filling level of the working medium. The cooling channel circuit is preferably hermetically and/or irreversibly sealed or sealable. In particular, the cooling channel circuit can be sealed after filling of the cooling channel circuit. The opening of the cooling channel circuit can be closed, for example, by soldering, welding, screwing and/or fusing. The working medium in the cooling channel circuit is, in particular, a fluid, which is preferably dielectric. The working medium can be, in particular, acetone, ethanol, water, methanol, fluorinated fluids, such as Novec, perfluorohexane, for example FC-72, a solvent, a coolant or a composite of said substances.

Alternatively or in addition, the part of the cooling element block in contact with the working medium or the entire cooling element block can be constructed from an electrically insulating material, for example from the polymer. Depending on the configuration, the two-phase cooling system can advantageously guarantee the electrical insulation between heat source and heat sink therefore, whereas additional component parts are frequently required for this in the case of a conventional cooling system, in particular when copper and/or aluminum cooling element blocks are used.

One embodiment provides that a cooling capacity of the working medium circulating in the cooling channel circuit during operation is greater than a cooling capacity of the cooling element block surrounding the cooling channel circuit. In other words, the two-phase cooling system is configured in such a way that the heat transport in the cooling channel circuit inside the cooling element block preferably significantly exceeds the heat conduction of the cooling element block.

One embodiment provides that a channel wall of the cooling element block enclosing the working medium in the cooling channel circuit is composed of an electrically insulating material, for example a polymer or a ceramic, in particular if the cooling element block is composed of metal. The channel wall is in particular diffusion-resistant. The channel wall has, in particular, a dielectric strength greater than 4 kV/mm, preferably greater than 80 kV/mm. This embodiment is advantageous in particular because the electrical insulation between the remaining regions of the cooling element block and the working medium occurs via the channel wall. There is consequently greater choice for the material composition of the two-phase cooling system.

One embodiment provides that the cooling element block has an insert, in particular made of copper and/or aluminum, wherein the material of the insert has a higher thermal conductivity than the material of the cooling element block. The insert can be impermeable or porous. In particular if the cooling element block has, for example, the ceramic and/or preferably the polymer, the insert can be thermally directly coupled particularly flexibly to the cooling element block. The insert can be, for example, completely or partially enclosed by the cooling element block. Alternatively, the insert can be placed on the cooling element block. The insert advantageously makes improved thermal coupling between the different components, in particular between the heat sink, the heat source, the cooling element block and/or the cooling channel circuit possible. Basically it is conceivable that the cooling element block has a plurality of inserts or that the insert is composed of a plurality of, in particular structurally identical, insert elements.

One embodiment provides that the cooling element block has a further cooling channel circuit and that the cooling channel circuit and the further cooling channel circuit are thermally directly coupled via the insert. The cooling channel circuit and the further cooling channel circuit can, in principle, have similar characteristics, for example can be constructed from identical channel sections. Basically it is conceivable that the character, for example a cross-section, a working medium, an arrangement, etc., of the channel sections of the cooling channel circuit and of the further cooling channel circuit differs. The working medium of the cooling channel circuit and the working medium of the further cooling channel circuit are, in particular, separated from each other, for example separated from each other by the insert and optionally also by the channel walls. The respective closed paths typically do cross therefore, so the respective working media are not mixed. By way of the thermally direct coupling, the insert advantageously makes a heat transfer from the cooling channel circuit into the further cooling channel circuit possible, and vice versa. In this configuration, the heat source is typically facing the cooling channel circuit and the heat sink facing the further cooling channel circuit. The insert is arranged, in particular, between a channel section of the cooling channel circuit and a channel section of the further cooling channel circuit.

One embodiment provides that the cooling channel circuit and the further cooling channel circuit lie in different geometric planes respectively, wherein the planes have a spacing greater than zero and at least one extent of the insert correlates with the value of the spacing in order to thermally bridge the spacing between the cooling channel circuit and the further cooling channel circuit, wherein the cooling channel circuit and the further cooling channel circuit are thermally directly coupled via the insert. The two planes are, in particular, oriented parallel to each other. The two planes are spanned, in particular, by the respective channel sections of the cooling channel circuits. The embodiment advantageously makes a construction of the two-phase cooling system over a plurality of planes and/or in a plurality of layers possible, with the respective cooling channel circuits being thermally directly coupled via the insert and optionally further inserts. This embodiment offers the advantage therefore that an effect of gravitation or a centrifugal force on the working medium and an accompanying cooling capacity limitation can be reduced, and can preferably be ruled out. For this, it can be advantageous in particular to orient at least one plane, in particular the planes tangential and/or perpendicular to the direction of gravitation and/or to the direction of centrifugal force. The centrifugal force can result, for example, due to the use of the X-ray high-voltage generator on a rotating part of the gantry of a computed tomography facility.

One embodiment provides that the two-phase cooling system has a supporting element for starting the two-phase cooling system, in particular the heat pipe. The following five embodiments each describe such a supporting element, which are suitable individually or considered in any combination respectively for improving starting of the two-phase cooling system. The improvement can lie in an increase in the probability that the two-phase cooling system has started.

Starting of the two-phase cooling system comprises, in particular, starting of the heat pipe and/or means that the working medium flows inside the cooling channel circuit. In this application, "during operation of the two-phase cooling system" is defined as the working medium flowing. The two-phase cooling system is thus ready for heat dissipation. In other words, the two-phase cooling system dissipates heat as soon as the startup procedure starts. In order to start, the two-phase cooling system typically has to absorb heat. The heat dissipation, in particular the cooling effect, frequently begins in the process. Starting occurs, in particular, as soon as a there is temperature difference between the heat source and the heat sink. Before operation of the X-ray high-voltage generator the two-phase cooling system can basically be inoperative, and this means that in the meantime the working medium does not flow in the cooling channel circuit. The two-phase cooling system is preferably started before or as soon as the at least one power electronics circuit part forms the heat source.

One embodiment provides that the insert is arranged inside the cooling channel circuit and the working medium flows around it and the insert acts as a supporting element for starting the two-phase cooling system. In this embodiment, the insert can be impermeable or porous, for example a metal foam. The insert is arranged, in particular, adjacent to the heat source and/or to the heat sink. Adjacent means, in particular, that the insert can intensify the thermally direct coupling owing to the small distance from the heat source or heat sink.

One embodiment provides that the two-phase cooling system has a liquid reservoir as a supporting element, having an additional quantity of working medium, wherein the liquid reservoir is connected to the cooling channel circuit. The liquid reservoir can be provided in the cooling element block. The liquid reservoir is typically arranged adjacent to the cooling channel circuit. The additional quantity of working medium preferably supports starting of the two-phase cooling system.

One embodiment provides that as a supporting element the cooling channel circuit encloses an element for surface enlargement, for example a spiral spring and/or cooling fins. The element for surface enlargement can be constructed in accordance with the insert and/or be composed of the material of the insert. The element for surface enlargement intensifies, preferably in situ, the thermally direct coupling and thus supports starting of the two-phase cooling system.

One embodiment provides that as a supporting element the cooling channel circuit adjacent to the heat source has a tapered cross-section. In other words, the cooling channel circuit is tapered adjacent to the heat source. The cooling channel circuit can basically alternatively or additionally be tapered adjacent to the heat sink. The tapering of the cooling channel circuit advantageously intensifies the capillary effect and/or thus improves starting of the two-phase cooling system. The tapering of the cooling channel circuit means, in particular, a cross-sectional tapering in a segment of the cooling channel circuit.

One embodiment provides that as a supporting element the two-phase cooling system has an auxiliary heat source thermally directly coupled to the cooling channel circuit. The auxiliary heat source is typically an electrical component, for example a heating resistor, and/or inductive component. The auxiliary heat source can, in particular, be activated before the heat source is operative and/or before the X-ray beam is generated. After starting of the two-phase cooling system the auxiliary heat source is typically deactivated. The auxiliary heat source is activated, for example, in that it is switched on, in other words, is out into operation. The auxiliary heat source and the heat source can be operated alternately, for example. The auxiliary heat source can, in particular, be active in a period between provision of the high voltage and/or generation of the X-ray beams. The auxiliary heat source can basically be operative while the heat source is operative. The auxiliary heat source typically generates a lower power loss input, for example by a factor of 10, in particular a factor of 1,000, than the heat source. The auxiliary heat source typically generates only power loss. The auxiliary heat source is configured, in particular, by way of the generated power loss input to support starting of the two-phase cooling system, in particular starting of the heat pipe. The auxiliary heat source makes it possible, in particular, that the heat pipe starts or has started if the at least one power electronics circuit part is inoperative. The auxiliary heat source is typically arranged adjacent to the heat source and/or the heat sink. Basically it is conceivable that the auxiliary heat source is arranged on a segment of the cooling channel circuit at which the working medium is displaced by gravitation and/or the centrifugal force in order to preferably counteract the displacement.

One embodiment provides that the cooling channel circuit has an angled design such that at least two subplanes of the cooling channel circuit are at an angle of greater than 0° to each other. The angle is typically more than 0° and less than 360°. According to this embodiment, the cooling channel circuit is not completely planar, in other words, configured in a single plane, but has an angle, for example a kink, or a curve. In a side view or in a cross-section through the cooling channel circuit the cooling channel circuit can form, for example, an L, a U or an O. In the latter case, the cooling channel circuit is angled in such a way that the cooling channel circuit can form a kind of circle. A sub-plane of the cooling channel circuit comprises, in particular, those channel sections of the cooling channel circuit, which lie at least approximately in one geometric plane. If the cooling channel circuit forms, for example, an L, one of the two sub-planes is in the first leg of the L and the other of the two sub-planes is in the second leg of the L. Basically it is conceivable as a development of this embodiment that separate cooling channel circuits are provided in each sub-plane, and these are thermally directly coupled in pairs, for example via the insert. This embodiment is advantageous, in particular, because the two-phase cooling system can consequently be configured more flexibly spatially.

One embodiment provides that the at least one power electronics circuit part, as part of a channel wall of the cooling element block enclosing the working medium in the cooling channel circuit, is introduced into the cooling element block and the working medium is electrically insulating. The advantage of this embodiment is, in particular, that the working medium comes into direct contact with the power electronics circuit part, whereby the thermally direct coupling is typically intensified. Heat is thus typically dissipated from the heat source directly at the surface of the at least one power electronics circuit part. In this case, the working medium is electrically insulating to guarantee safe operation of the X-ray high-voltage generator.

One embodiment provides that the two-phase cooling system has a temporary heat accumulator, in particular made of copper and/or aluminum, wherein the temporary heat accumulator is thermally directly coupled to the at least one power electronics circuit part via a heat-distributing element and wherein the heat-distributing element adjoins the cooling channel circuit in a planar manner. The temporary heat accumulator is, for example, a metal block, in particular made of copper and/or aluminum. The temporary heat accumulator preferably makes buffering of a maximum power loss input by way of the heat source possible. The heat-distributing element is composed, in particular, of diamond and/or a graphitic material. By way of the planar adjacency the heat-distributing element typically enlarges the heat-transfer surface between the working medium and the at least one power electronics circuit part and thus improves the thermal direct coupling. The heat-distributing element can form the channel wall, in particular in a segment of the cooling channel circuit. The heat-distributing element can have a length, which correlates with the spacing between the temporary heat accumulator and the heat source.

An inventive X-ray tube assembly has
the X-ray high-voltage generator for providing a high voltage and
an X-ray tube for X-ray beam generation using the provided high voltage.

Since the X-ray tube assembly has the X-ray high-voltage generator, the X-ray tube assembly shares the advantages previously discussed in connection with the X-ray high-voltage generator and its embodiments. The X-ray tube assembly forms, in particular, an X-ray beam generating facility.

The X-ray tube typically has an evacuated X-ray tube housing, which encloses a high vacuum, an electron emitter and an anode. The anode can be a rotating anode or a stationary anode. With the design as a rotating anode, a distinction is typically made between a rotating anode X-ray tube, in which the anode rotates inside the X-ray tube housing, and a rotary piston X-ray tube, in which the node rotates together with the X-ray tube housing.

The electron emitter is, in particular, a field effect emitter or a thermionic emitter. The field effect emitter typically has carbon nanotubes or silicon nanotubes or molybdenum nanotubes. The electron emission with the field effect emitter is typically effected by applying a gate voltage, which by way of the electrical field occurring in the peaks of the nanotubes extracts the electrons from these nanotubes, whereby the electron emission current is formed. In addition or as an alternative to switching via the gate voltage, a generated electron emission current can be blocked via a barrier grid. A current limiting unit can be connected upstream of the nanotubes. The thermionic emitter is, for example, a spiral emitter or a flat emitter, which can be heated directly or indirectly.

The electron emitter is designed as a cathode or arranged together with a cathode opposite the anode. The provided high voltage is applied between the cathode and the anode. The X-ray high-voltage generator is connected to the X-ray tube in order to transfer the provided high voltage. The electrons emitted by the electron emitter are accelerated via the high voltage in the direction of the anode and on interaction the X-ray radiation is generated on the anode in a focal spot.

The generated X-ray beams can be used, in particular, for medical imaging and/or materials testing. Typical applications in medical imaging are angiography, computed tomography, fluoroscopy, imaging for radiotherapy, mammography and/or radiography. The X-ray tube assembly is frequently used in combination with an X-ray detector. In addition, depending on the type of application, it can be integrated in an imaging system with, for example, a C-arm, a computed tomography system, etc.

An inventive computed tomography facility has a circular gantry having a rotating part and a stationary part and the X-ray high-voltage generator or the X-ray tube assembly having the X-ray high-voltage generator, wherein the two-phase cooling system is arranged on the gantry.

Since the computed tomography facility has the X-ray high-voltage generator, the computed tomography facility shares the advantages previously discussed in connection with the X-ray high-voltage generator and its embodiments.

One embodiment provides that the two-phase cooling system is arranged on the rotating part and the two-phase cooling system is oriented in such a way that a plane of the cooling channel circuit forms a tangent in relation to the circular gantry. The cooling channel circuit with the working medium is in particular perpendicular to a radius of the circular gantry. The rotating part of the gantry is typically spaced apart from the stationary part in an air gap. The power for operating the high voltage generator and thus the X-ray tube assembly is transferred from the stationary part to the rotating part via this air gap, for example with or without contact. In the reverse direction, for example data of the X-ray detector is transferred preferably without contact, for example electrostatically, capacitively or optically.

This embodiment is advantageous, in particular, because an effect of the centrifugal force acting on the working medium on rotation of the rotating part can be reduced, preferably minimized. Adequate heat dissipation from the X-ray high-voltage generator during operation of the computed tomography facility is consequently advantageously guaranteed.

DETAILED DESCRIPTION

Figure 1:
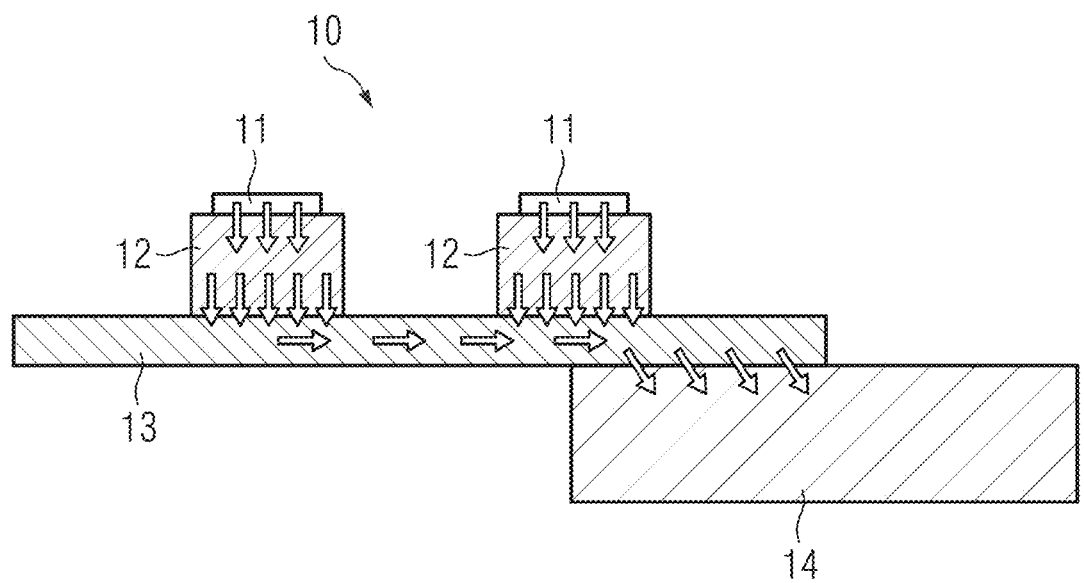
FIG. 1 shows a conventional X-ray high-voltage generator according to the prior art.

FIG. 1 shows a conventional X-ray high-voltage generator 10 according to the prior art.

As part of a circuit arrangement for providing a high voltage the X-ray high-voltage generator 10 has two power electronics circuit parts 11 as heat sources. The two power electronics circuit parts 11 are each arranged on a cooling element block 12, which is composed, for example, of copper. A carrier plate 13 carries the two cooling element blocks 12 and connects them to a heat sink 14. The carrier plate 13 can be electrically insulating. Alternatively or in addition, an insulation layer for electrical insulation of the power electronics circuit parts 11 can be provided as part of the conventional X-ray high-voltage generator 10. The arrows denote the heat flow from the heat sources to the heat sink 14.

Figure 2:
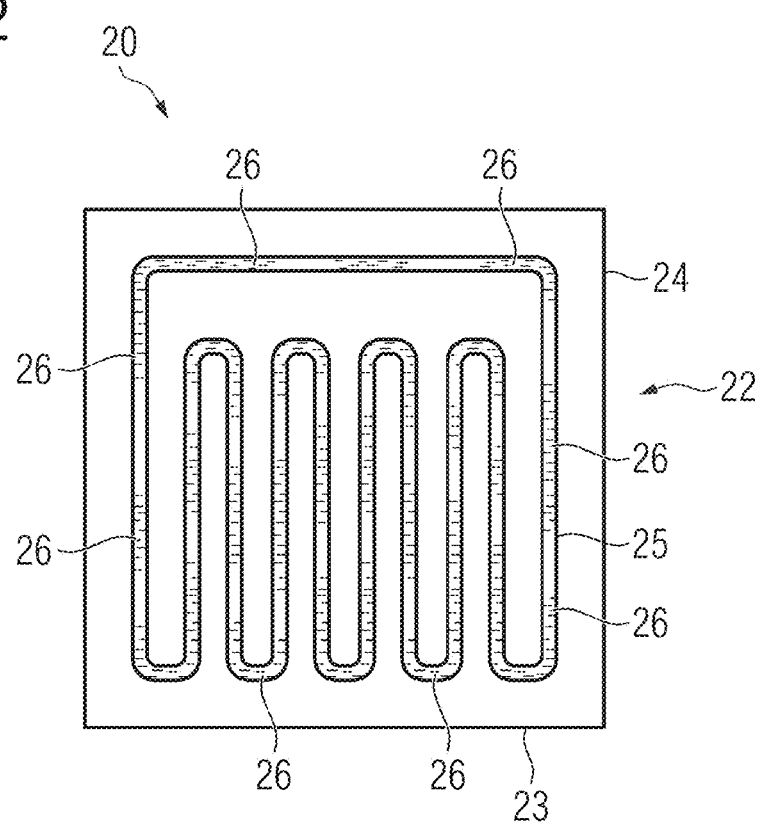
FIG. 2 shows an inventive X-ray high-voltage generator.

FIG. 2 shows a detail of an inventive X-ray high-voltage generator 20.

The X-ray high-voltage generator 20 is designed for providing a high voltage for X-ray beam generation in an X-ray tube. The X-ray high-voltage generator 20 has a circuit arrangement having at least one power electronics circuit part 21 and a two-phase cooling system 22. During operation the at least one power electronics circuit part 21 forms a heat source. It is basically conceivable that the X-ray high-voltage generator 20 has a carrier plate (not shown) for further stabilization of the X-ray high-voltage generator 20.

The two-phase cooling system 22 has a heat sink 23 or acts as a heat sink 23 itself on the sides remote from the heat source. The at least one power electronics circuit part 21 is directly thermally coupled to the two-phase cooling system 22 for dissipating heat from the heat source at the heat sink 23. For this, the two-phase cooling system 22 has a cooling element block 24. The cooling element block 24 spatially surrounds a cooling channel circuit 25. The cooling channel circuit 25 is part of the two-phase cooling system 22. The cooling channel circuit 25 is filled at least partially with a working medium 26 and acts as a heat pipe.

Purely for illustrative purposes the cooling channel circuit 25 has channel sections arranged in a meandering manner. By way of example, 10 parallel channel sections are shown. The number of parallel channel sections can lie above 50, in particular above 500, for example between 2 and 1,000. A spacing, in other words, a web width, between the channel sections is typically between 0.01 and 5 mm, for example between 0.1 and 1 mm. If the cooling element block 24 is composed of polymer, the web width is, for example, at least 0.3 mm, preferably 0.5 mm.

In a preferred development, a cooling capacity of the working medium 26 circulating in the cooling channel circuit 25 during operation is greater than a cooling capacity of the cooling channel circuit 25 surrounding cooling element block 24.

FIG. 2 shows a cross-section along a plane of the cooling channel circuit 25. The cutting plane A-A is indicated in FIG. 8. In the following FIGS. 3 to 15, this plane of the cooling channel circuit 25 is substantially perpendicular to the drawing sheet plane compared to FIG. 2.

Figure 3:
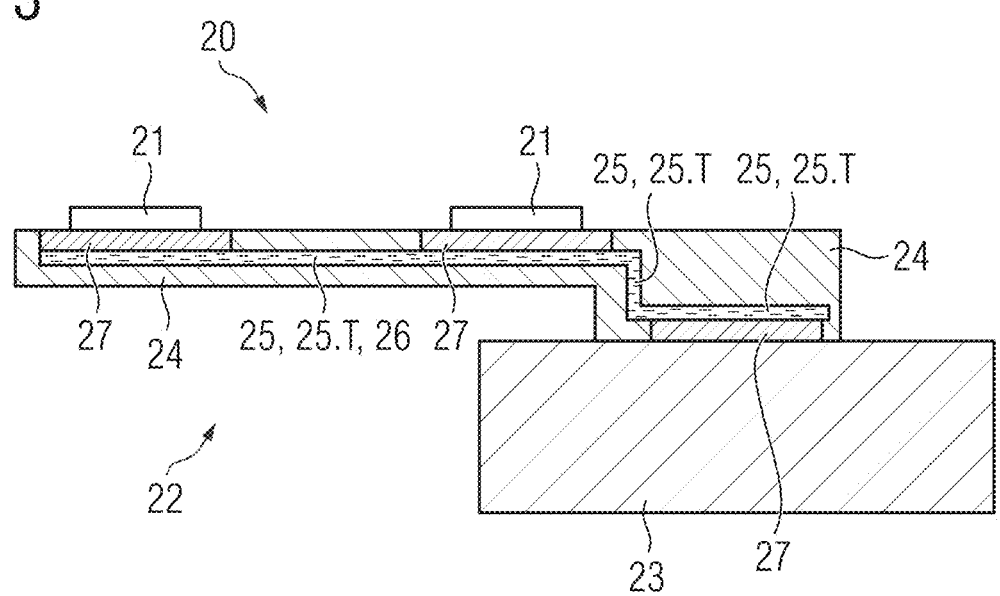
FIG. 3 shows a first exemplary embodiment of the X-ray high-voltage generator.

FIG. 3 shows a first exemplary embodiment of the X-ray high-voltage generator 20.

In this exemplary embodiment, the X-ray high-voltage generator 20 has two power electronics circuit parts 21.

The cooling element block 24 has an insert 27, in particular made of copper and/or aluminum. The material of the insert 27 has a higher thermal conductivity than the material of the cooling element block 24. In this exemplary embodiment, the insert 27 is composed of a plurality of insert elements. The at least one power electronics circuit part 21 and the heat sink 23 are each directly thermally coupled to the cooling channel circuit 25 via an insert element. An insulation layer 38 (not shown) can be used for electrical insulation.

A supporting apparatus of the X-ray high-voltage generator 20 having an appropriate mass and thermal capacity is connected to the cooling element block 24 and thermally directly coupled to further improve the cooling capacity. The supporting apparatus in particular consequently forms the heat sink 23 of the two-phase cooling system 22. The supporting apparatus can be, for example, a housing of the X-ray high-voltage generator 20 or a gantry of a computed tomography facility or a frame of an X-ray tube assembly 40 (not represented in FIG. 3).

The cooling channel circuit 25 has an angled design such that at least two, in this exemplary embodiment three, sub-planes 25.T of the cooling channel circuit 25 are at an angle of greater than 0° to each other. The two angles shown in FIG. 3 are approximately 90°.

Figure 4:
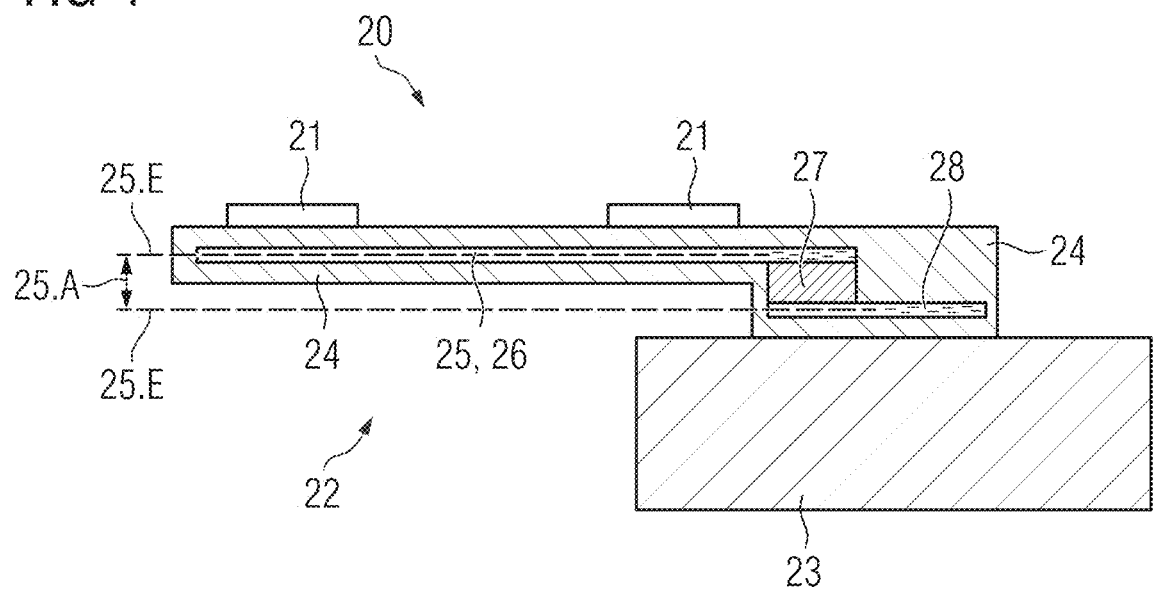
FIG. 4 shows a second exemplary embodiment of the X-ray high-voltage generator.

FIG. 4 shows a second exemplary embodiment of the X-ray high-voltage generator 20.

In this exemplary embodiment, the cooling element block 24 has the insert 27. The cooling element block 24 has a further cooling channel circuit 28 in addition to the cooling channel circuit 25. The cooling channel circuit 25 and the further cooling channel circuit 28 are thermally directly coupled via the insert 27. The cooling channel circuit 25 and the further cooling channel circuit 28 each lie in different geometric planes 25.E. The planes 25.E have a spacing 25.A greater than zero. At least one extent of the insert 27 correlates with the value of the spacing 25.A in order to thermally bridge the spacing 25.A between the cooling channel circuit 25 and the further cooling channel circuit 28. The cooling channel circuit 25 and the further cooling channel circuit 28 are directly thermally coupled via the insert 27.

Figure 5:
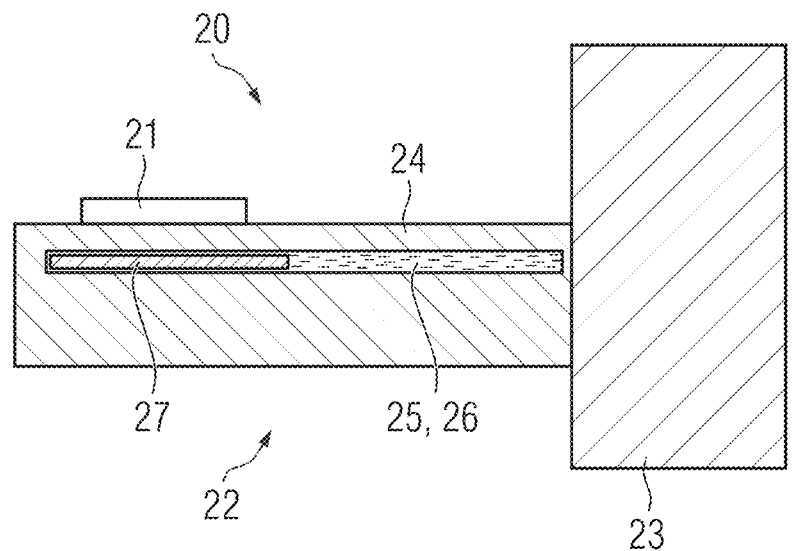
FIG. 5 shows a third exemplary embodiment of the X-ray high-voltage generator.

FIG. 5 shows a third exemplary embodiment of the X-ray high-voltage generator 20.

In this exemplary embodiment, the cooling element block 24 has the insert 27. The insert 27 is arranged inside the cooling channel circuit 25 and the working medium 26 flows around it. The insert 27 can be designed to be impermeable or porous, for example as a metal foam. An insert 27 designed in this way typically supports starting of the two-phase cooling system 22 and thus acts as a supporting element for starting the two-phase cooling system 22.

In this embodiment, a channel wall of the cooling element block 24 enclosing the working medium 26 in the cooling channel circuit 25 can be advantageously composed of an electrically insulating material, for example a polymer or a ceramic.

Figure 6:
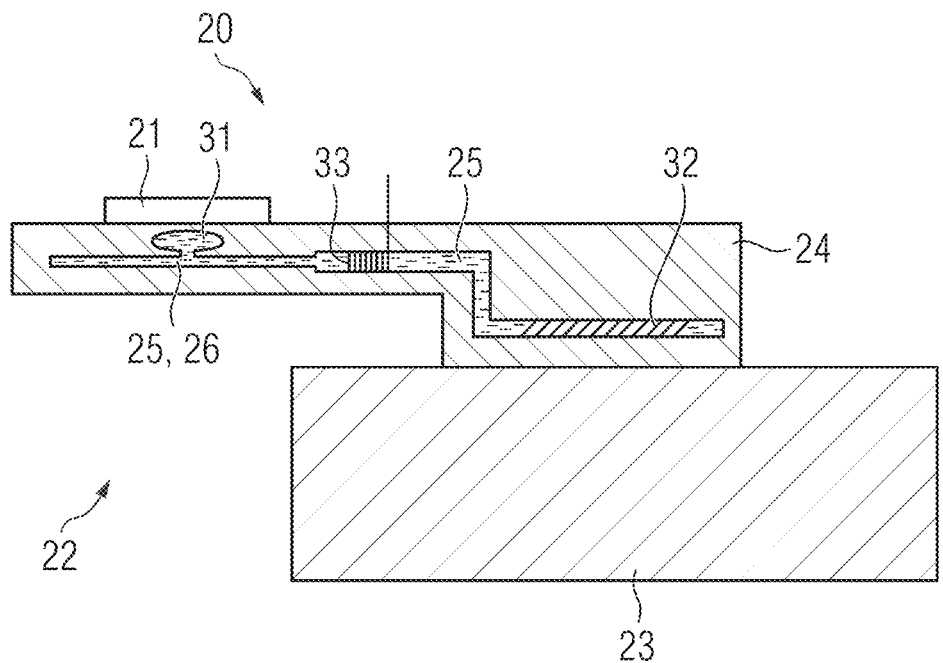
FIG. 6 shows a fourth exemplary embodiment of the X-ray high-voltage generator.

FIG. 6 shows a fourth exemplary embodiment of the X-ray high-voltage generator 20.

This exemplary embodiment shows four further embodiments of a supporting element for starting of the two-phase cooling system 22, which can serve individually or in combination, in particular as a development or an alternative to the exemplary embodiment shown in FIG. 5, to support starting of the two-phase cooling system 22. In other words, each of these variants can be combined with each other or used individually to achieve the technical effect or in combination to intensify it.

Firstly: The two-phase cooling system 22 has as a supporting element a liquid reservoir 31 having an additional quantity of working medium 26. The liquid reservoir 31 is connected to the cooling channel circuit 25. The liquid reservoir 31 is preferably directly thermally coupled to the heat source, for example arranged underneath the heat source.

Secondly: The cooling channel circuit 25 encloses an element for surface enlargement 32 as a supporting element. In this exemplary embodiment, the element for surface enlargement 32 is a spiral spring, which is arranged adjacent to the heat sink 23.

Thirdly: The two-phase cooling system 22 has as a supporting element an auxiliary heat source 33 thermally directly coupled to the cooling channel circuit 25.

Fourthly: The cooling channel circuit 25 has a tapered cross-section adjacent to the heat source.

Figure 7:
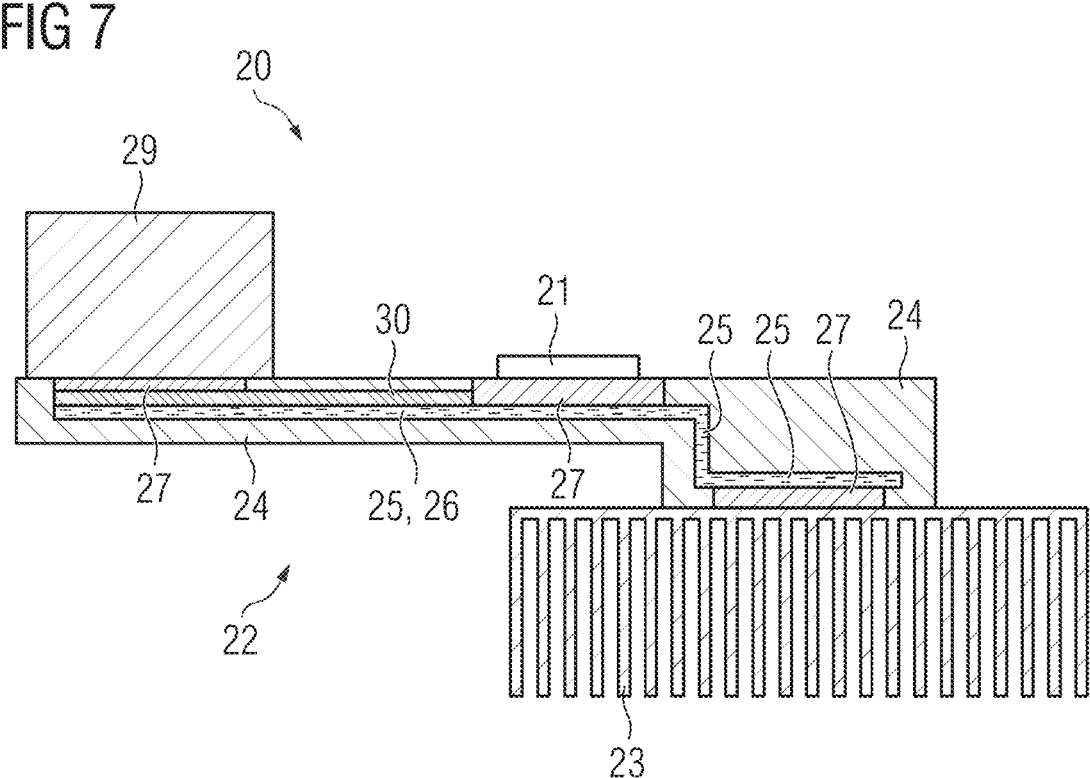
FIG. 7 shows a fifth exemplary embodiment of the X-ray high-voltage generator.
Figure 8:
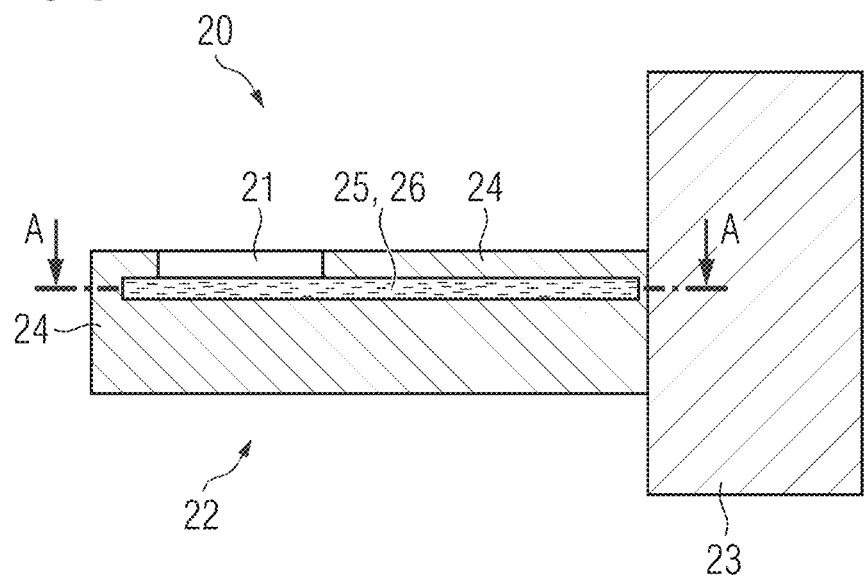
FIG. 8 shows a sixth exemplary embodiment of the X-ray high-voltage generator.

FIG. 7 shows a fifth exemplary embodiment of the X-ray high-voltage generator 20.

The two-phase cooling system 22 has a temporary heat accumulator 29, in particular made of copper and/or aluminum. The temporary heat accumulator 29 is thermally directly coupled to the at least one power electronics circuit part 21 via a heat-distributing element 30, in particular made of diamond and/or a graphitic material. The heat-distributing element 30 adjoins the cooling channel circuit 25 in a planar manner. Basically an insert element can be provided between the heat-distributing element 30 and the temporary heat accumulator 29 and/or the at least one power electronics circuit part 21 and/or the heat sink 23.

In this exemplary embodiment, the cooling element block 24 has the insert 27, with the three insert elements thereof each thermally directly coupling the temporary heat accumulator 29, the at least one power electronics circuit part 21 and the heat sink 23 to the cooling channel circuit 25. In this exemplary embodiment, the heat sink 23 is fitted with a form, in particular cooling ribs, enlarging the surface.

The temporary heat accumulator 29 is arranged in this figure such that the at least one power electronics circuit part 21 is arranged between the temporary heat accumulator 29 and the heat sink 23. Alternatively it is conceivable that the temporary heat accumulator 29 is arranged between the at least one power electronics circuit part 21 and the heat sink 23. In this context "between" means, in particular, on the shortest section along the cooling channel circuit 25.

FIG. 8 shows a sixth exemplary embodiment of the X-ray high-voltage generator 20.

The at least one power electronics circuit part 21 is introduced as part of a channel wall of the cooling element block 24 enclosing the working medium 26 in the cooling channel circuit 25 into the cooling element block 24. The working medium 26 is electrically insulating.

Figure 9:
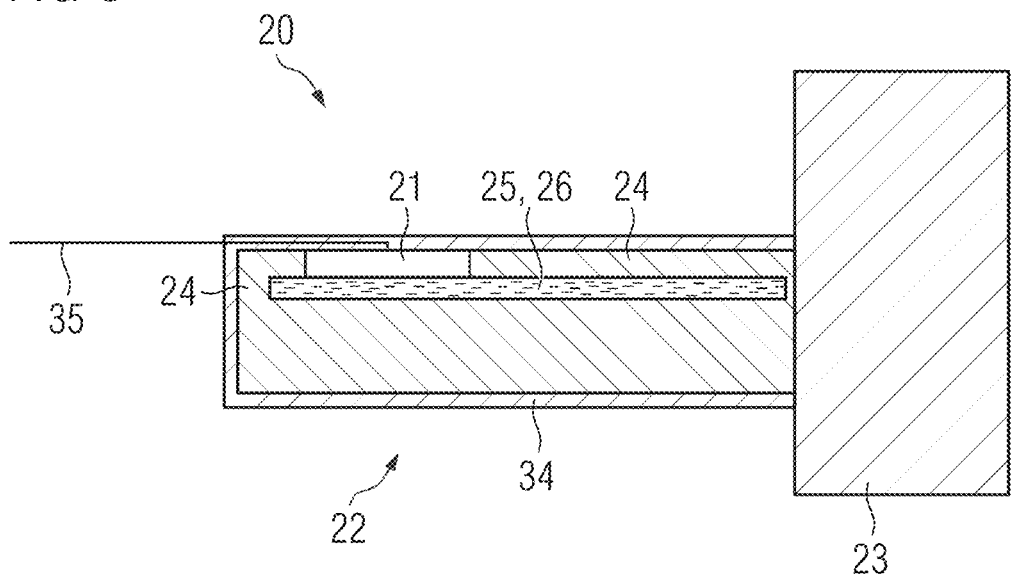
FIG. 9 shows a seventh exemplary embodiment of the X-ray high-voltage generator.

FIG. 9 shows a seventh exemplary embodiment of the X-ray high-voltage generator 20.

The cooling element block 24 is at least partially enveloped by a metal element 34, in particular by a printed circuit board. In this exemplary embodiment, the cooling element block 24 is completely enveloped by the metal element 34. The working medium 26 is electrically insulating. The metal element 34 is a printed circuit board in which a current supply 35, for example for the at least one power electronics element 21, is integrated. The current supply 35 can form a layer of the printed circuit board. Basically it is conceivable that the current supply 35 is designed as a busbar. In this exemplary embodiment, the cooling element block preferably has the polymer. The metal element 34 seals the cooling element block 24.

Figure 10:
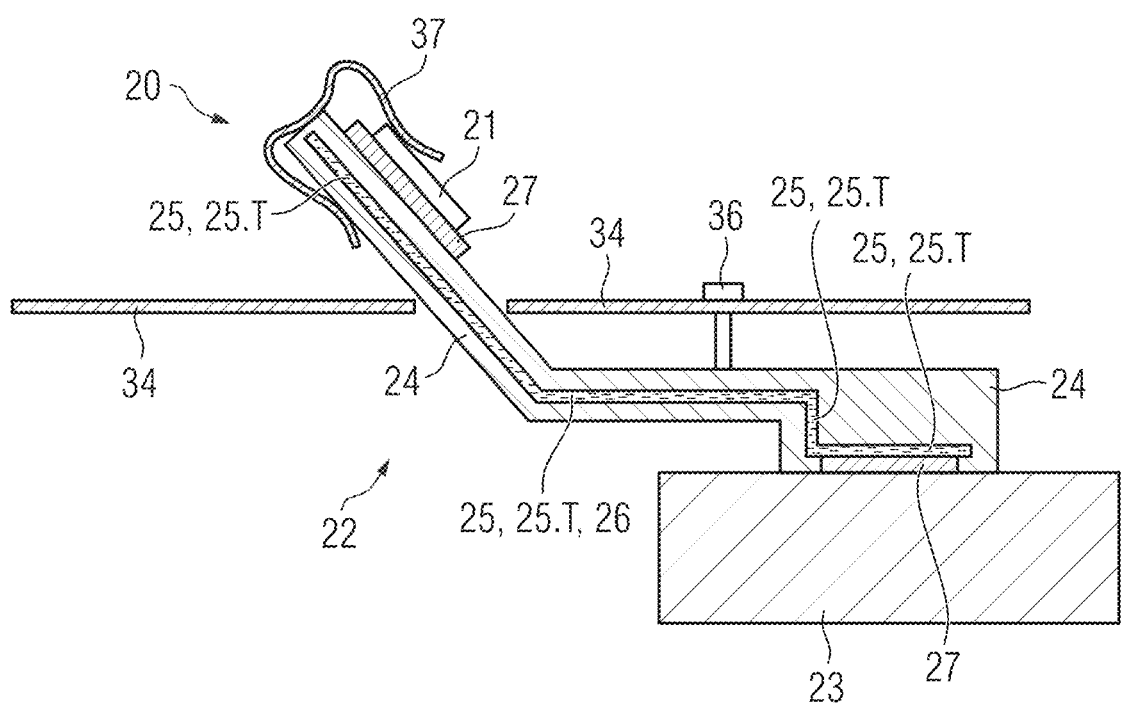
FIG. 10 shows an eighth exemplary embodiment of the X-ray high-voltage generator.

FIG. 10 shows an eighth exemplary embodiment of the X-ray high-voltage generator 20.

In this exemplary embodiment, the cooling element block 24 has the insert 27. The cooling channel circuit 25 has an angular design such that at least two, in this exemplary embodiment four, sub-planes 25.T of the cooling channel circuit 25 are at an angle of greater 0° to each other.

In addition, FIG. 10 shows that a fixing element 37, such as a type of spring element, is used for fixing the at least one power electronics circuit part 21 on the two-phase cooling system 22. The metal element 34 is fixed to the cooling element block 24 with a holding apparatus 36. The holding apparatus 36 is, for example, a screw and/or a bracket.

The cooling element block 24 offers the advantage that, due to the angled orientation, geometrically complex built-on accessories of the X-ray high-voltage generator 20 can be achieved, for example through a recess of the metal element 34.

Figure 11:
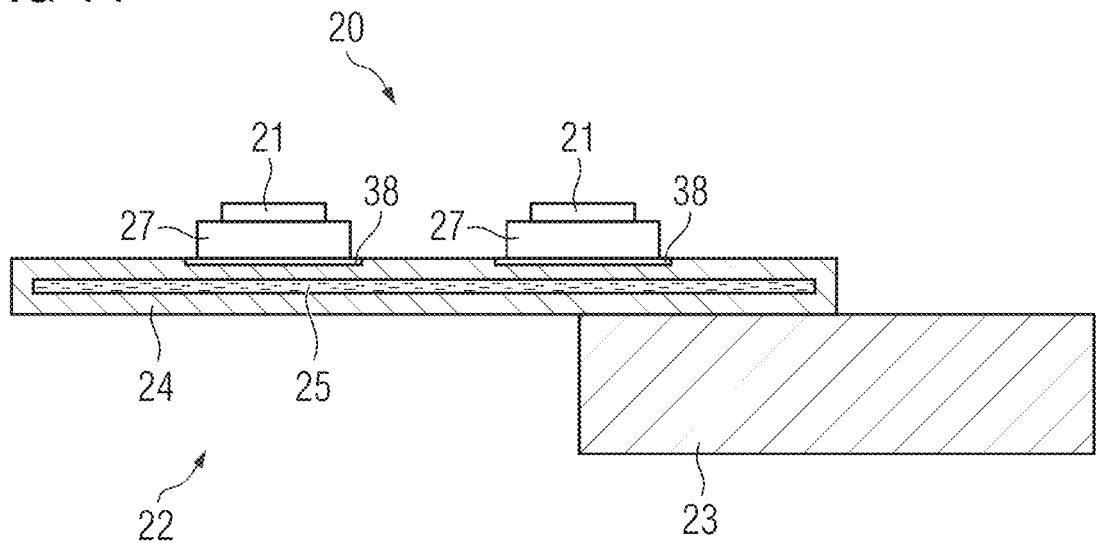
FIG. 11 shows a ninth exemplary embodiment of the X-ray high-voltage generator.

FIG. 11 shows a ninth exemplary embodiment of the X-ray high-voltage generator 20. This embodiment is inspired by the exemplary embodiment shown in FIG. 1 from the prior art with regard to the dimensioning of the component parts.

The cooling element block 24 is composed of a metal. An insulation layer 38 for electrical insulation is provided between the cooling element block 24 and the two power electronics circuit parts 21, therefore.

The insert 27 has two insert elements auf, which are designed and arranged in the manner of the cooling element blocks 12 known from the prior art (see FIG. 1). Owing to the improved heat dissipation via the two-phase cooling system 22, the insert 27 can be smaller than previously, and this entails cost and/or installation space and/or weight advantages.

Figure 12:
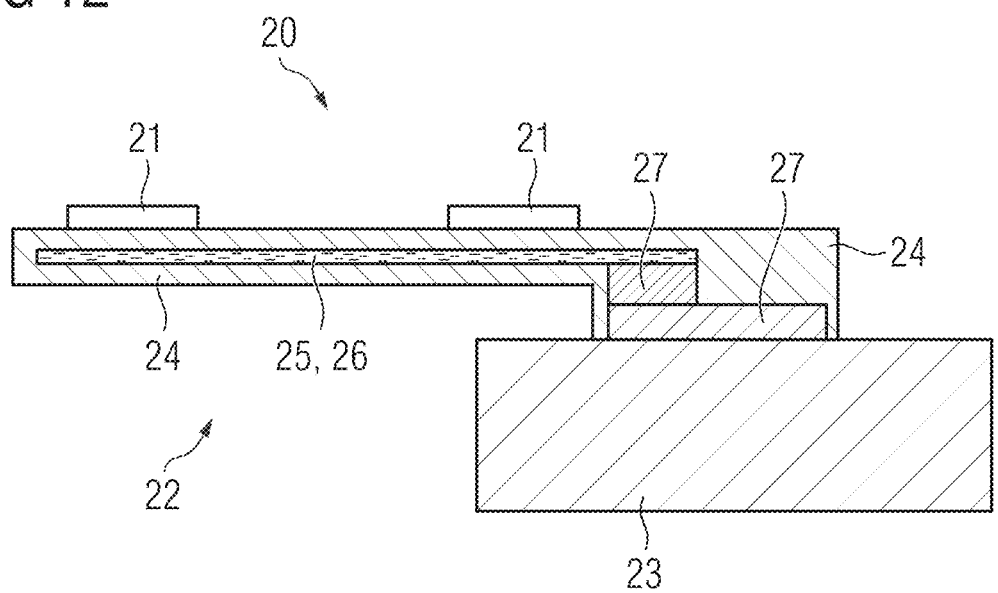
FIG. 12 shows a tenth exemplary embodiment of the X-ray high-voltage generator.

FIG. 12 shows a tenth exemplary embodiment of the X-ray high-voltage generator 20. This exemplary embodiment is substantially a development of the exemplary embodiment shown in FIG. 4.

The insert 27 has two insert elements, with the additional insert element compared to FIG. 4 replacing the second cooling channel circuit 28 to intensify the thermal coupling to the heat sink 23.

Figure 13:
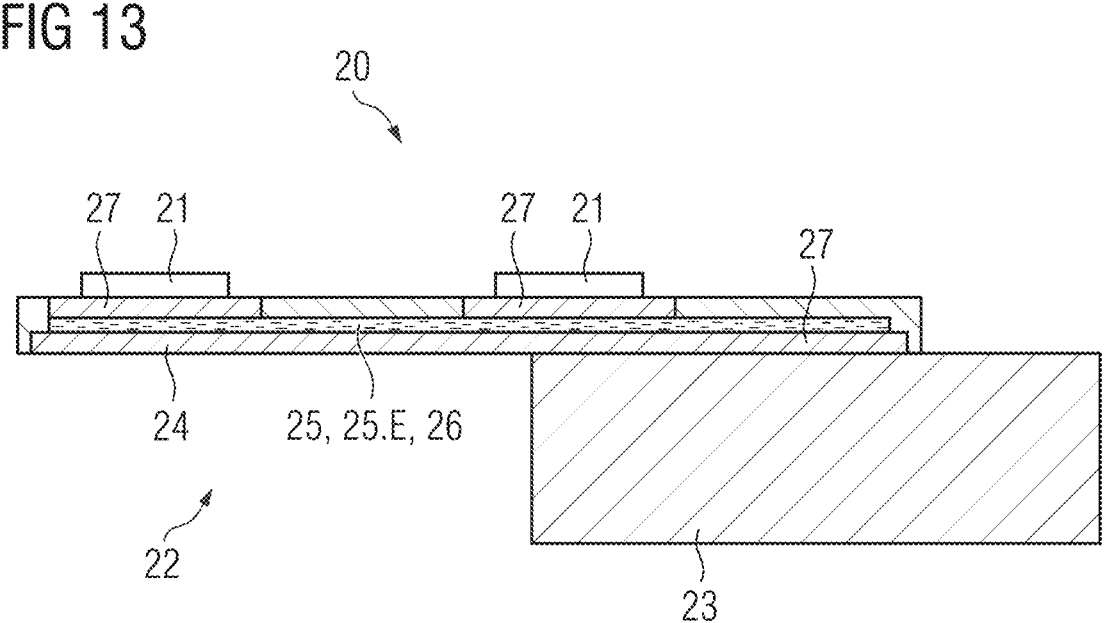
FIG. 13 shows an eleventh exemplary embodiment of the X-ray high-voltage generator.

FIG. 13 shows an eleventh exemplary embodiment of the X-ray high-voltage generator 20.

The cooling channel circuit 25 is planar in design and thus has only a single plane 25.E. The cooling channel circuit 25 is sealed at one side of the plane 25.E with one of the three insert elements of the insert 27 and adjoins the heat sink 23 in a planar manner.

Figure 14:
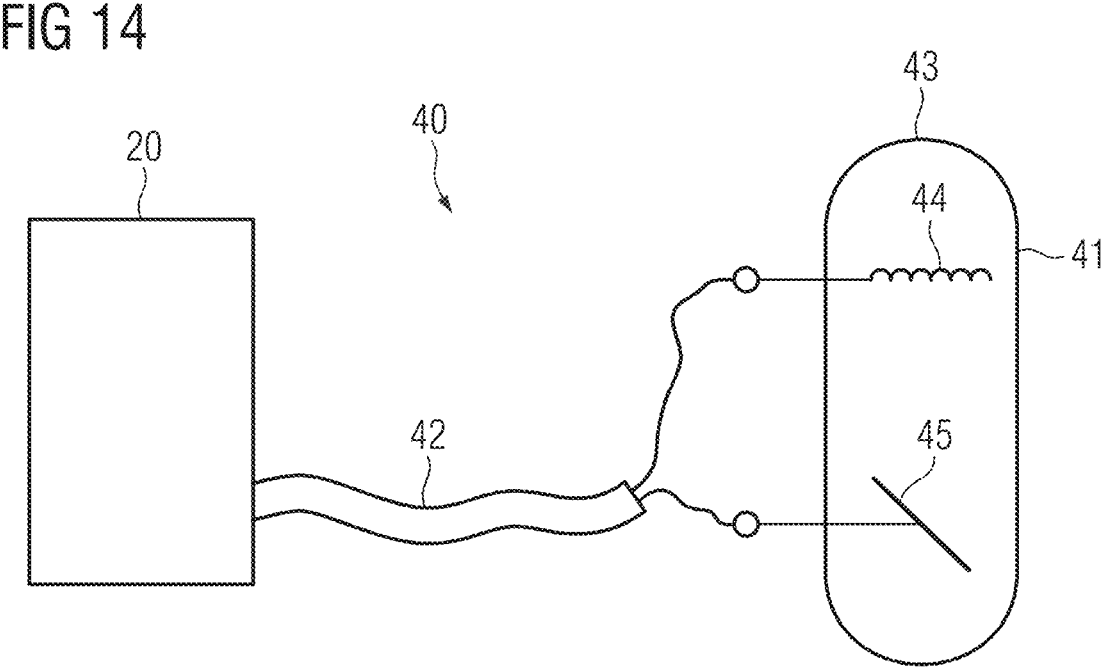
FIG. 14 shows an inventive X-ray tube assembly and FIG. 15 shows an inventive computed tomography facility.

FIG. 14 shows an inventive X-ray tube assembly 40.

The X-ray tube assembly 40 has an X-ray high-voltage generator 20 for providing a high voltage and an X-ray tube 41. The X-ray high-voltage generator 20 and the X-ray tube 41 are connected to a high voltage cable 42 for transferring the high voltage.

The X-ray tube 42 has an X-ray tube housing 43, an electron emitter 44 arranged therein as a cathode and an anode 45. The high voltage is applied between the electron emitter 44 and the anode 45.

Figure 15:
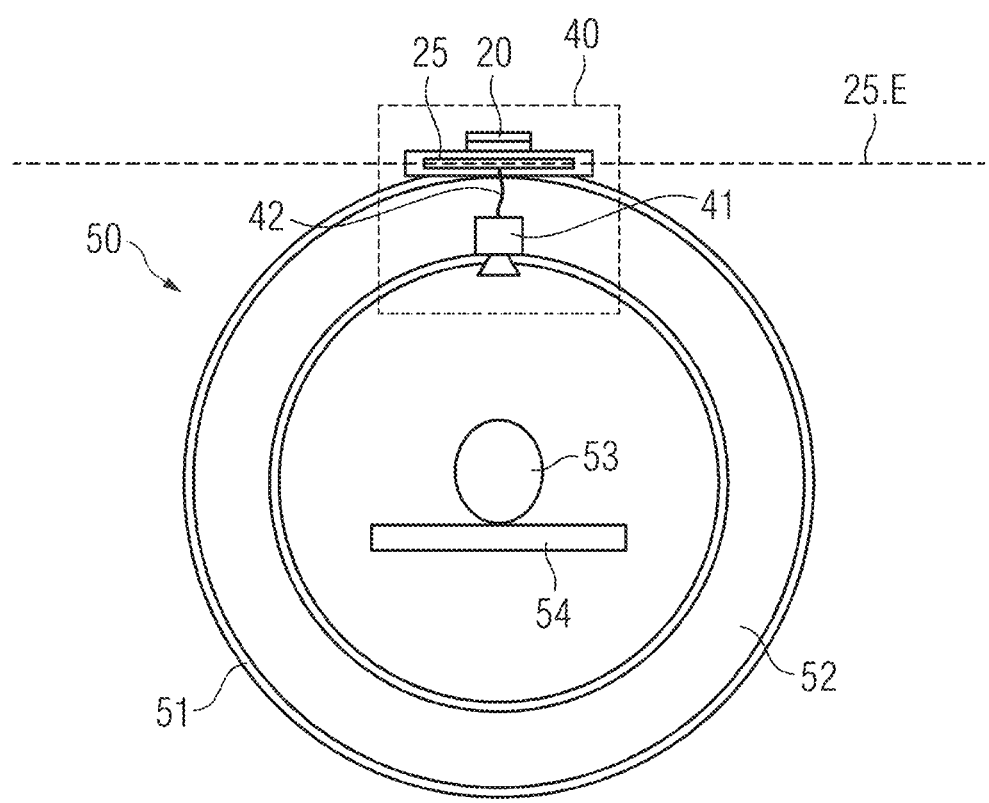

FIG. 15 shows a computed tomography facility 50.

The computed tomography facility 50 has a circular gantry having a rotating part 52 and a stationary part 51 as well as the X-ray high-voltage generator 20 as part of the X-ray tube assembly 40. In this exemplary embodiment, the rotating part 52 and the stationary part 51 are disk-shaped. Alternatively, a drum-shaped design may be considered.

The two-phase cooling system 22 is arranged on the gantry. The two-phase cooling system 22 is arranged on the rotating part 52. The two-phase cooling system 22 is oriented in such a way that a plane 25.E of the cooling channel circuit 25 forms a tangent in relation to the circular gantry.

In this exemplary embodiment, in particular the gantry forms the heat sink 23. In particular, a surface of the gantry acts as a heat sink 23, while the structural body of the gantry acts as a kind of temporary heat accumulator for the surface.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s)

as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

Although the present invention has been illustrated and described in detail by the preferred exemplary embodiments, it is nevertheless not limited by the disclosed examples and a person skilled in the art can derive other variations herefrom without departing from the scope of the present invention.

What is claimed is:

1. An X-ray high-voltage generator for providing a high voltage for X-ray beam generation in an X-ray tube, the X-ray high-voltage generator comprising:
    a circuit arrangement having at least one power electronics circuit part, wherein the at least one power electronics circuit part is configured to form a heat source during operation; and
    a two-phase cooling system having a heat sink, wherein
        the at least one power electronics circuit part is directly thermally coupled to the two-phase cooling system to dissipate heat from the heat source at the heat sink,
        the two-phase cooling system has a cooling element block,
        the cooling element block spatially surrounds a cooling channel circuit, and
        the cooling channel circuit is at least partially filled with a working medium, and is configured to act as a heat pipe.

2. The X-ray high-voltage generator as claimed in claim 1, wherein a cooling capacity of the working medium circulating in the cooling channel circuit during operation is greater than a cooling capacity of the cooling element block surrounding the cooling channel circuit.

3. The X-ray high-voltage generator as claimed in claim 1, wherein a channel wall of the cooling element block enclosing the working medium in the cooling channel circuit is composed of an electrically insulating material, and wherein the electrically insulating material is a polymer or a ceramic.

4. The X-ray high-voltage generator as claimed in claim 1, wherein the cooling element block has an insert, wherein a material of the insert has a higher thermal conductivity than a material of the cooling element block, and wherein the material of the insert is made of at least one of copper or aluminum.

5. The X-ray high-voltage generator as claimed in claim 4, wherein the cooling element block comprises:
a further cooling channel circuit, wherein
the cooling channel circuit and the further cooling channel circuit are thermally directly coupled via the insert.

6. The X-ray high-voltage generator as claimed in claim 5, wherein the cooling channel circuit and the further cooling channel circuit are arranged in different respective geometric planes, wherein the different respective geometric planes have a spacing greater than zero and at least one extent of the insert correlates with a value of the spacing to thermally bridge the spacing between the cooling channel circuit and the further cooling channel circuit.

7. The X-ray high-voltage generator as claimed in claim 4, wherein the insert is arranged inside the cooling channel circuit and configured such that the working medium flows around the insert, and wherein the insert is configured to act as a supporting element for starting the two-phase cooling system.

8. The X-ray high-voltage generator as claimed in claim 1, wherein the two-phase cooling system comprises:
one or more supporting elements configured to start the two-phase cooling system, wherein start of the two-phase cooling system includes starting the heat pipe.

9. The X-ray high-voltage generator as claimed in claim 8, wherein the one or more supporting elements include a liquid reservoir with an additional quantity of the working medium, and wherein the liquid reservoir is connected to the cooling channel circuit.

10. The X-ray high-voltage generator as claimed in claim 8, wherein the one or more supporting elements enclose an element for surface enlargement, the element including at least one of a spiral spring or cooling fins.

11. The X-ray high-voltage generator as claimed in claim 8, wherein the one or more supporting elements include an auxiliary heat source thermally directly coupled to the cooling channel circuit.

12. The X-ray high-voltage generator as claimed in claim 8, wherein, as the one or more supporting elements, the cooling channel circuit adjacent to the heat source has a tapered cross-section.

13. An X-ray tube assembly, comprising:
the X-ray high-voltage generator as claimed in claim 1, to provide the high voltage; and
an X-ray tube configured to generate X-ray beams using the high voltage.

14. A computed tomography facility, comprising:
the X-ray high-voltage generator as claimed in claim 1; and
a circular gantry including a rotating part and a stationary part, wherein the two-phase cooling system is arranged on the circular gantry.

15. The computed tomography facility as claimed in claim 14, wherein the two-phase cooling system is arranged on the rotating part and the two-phase cooling system is oriented such that a plane of the cooling channel circuit forms a tangent in relation to the circular gantry.

16. The X-ray high-voltage generator as claimed in claim 1, wherein a channel wall of the cooling element block enclosing the working medium in the cooling channel circuit is composed of an electrically insulating material is a polymer or a ceramic.

17. The X-ray high-voltage generator as claimed in claim 1, wherein the cooling element block has an insert, and wherein a material of the insert has a higher thermal conductivity than a material of the cooling element block.

18. The X-ray high-voltage generator as claimed in claim 6, wherein the insert is arranged inside the cooling channel circuit and configured such that the working medium flows around the insert, and wherein the insert is configured to act as a supporting element for starting the two-phase cooling system.

19. The X-ray high-voltage generator as claimed in claim 8, wherein the one or more supporting elements enclose an element for surface enlargement.

20. A computed tomography facility, comprising:
the X-ray tube assembly as claimed in claim 13; and
a circular gantry including a rotating part and a stationary part, wherein the two-phase cooling system is arranged on the circular gantry.

* * * * *